(12) United States Patent
Olsen et al.

(10) Patent No.: US 7,017,576 B2
(45) Date of Patent: Mar. 28, 2006

(54) BREATHING ASSISTANCE APPARATUS

(75) Inventors: Gregory James Olsen, Auckland (NZ); Martin Leckie, Auckland (NZ); Neil Prime, Auckland (NZ); Lewis George Gradon, Auckland (NZ); Nicholas Charles Alan Smith, Auckland (NZ); Alastair Edwin McAuley, Auckland (NZ); Mark Joseph Haycock, Auckland (NZ); Chris Earl Nightingale, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 10/646,434

(22) Filed: Aug. 22, 2003

(65) Prior Publication Data

US 2004/0035428 A1   Feb. 26, 2004

Related U.S. Application Data

(63) Continuation of application No. 10/072,271, filed on Feb. 7, 2002, now Pat. No. 6,789,541, which is a continuation-in-part of application No. 09/881,633, filed on Jun. 14, 2001, now Pat. No. 6,615,834.

(30) Foreign Application Priority Data

| Jun. 14, 2000 | (NZ) | ...... 505154 |
| Jun. 14, 2000 | (NZ) | ...... 505155 |
| Jun. 14, 2000 | (NZ) | ...... 505156 |
| Nov. 16, 2000 | (NZ) | ...... 508218 |
| Nov. 16, 2000 | (NZ) | ...... 508219 |
| Nov. 27, 2000 | (NZ) | ...... 508433 |
| Dec. 20, 2000 | (NZ) | ...... 509039 |
| Sep. 13, 2001 | (NZ) | ...... 514184 |

(51) Int. Cl.
*A62B 18/02* (2006.01)

(52) U.S. Cl. ............ 128/205.25; 128/206.24; 128/206.27; 128/207.11; 128/207.13

(58) Field of Classification Search .......... 128/206.24, 128/206.27, 207.11, 207.13, 207.17, 205.25
See application file for complete search history.

(56) References Cited

U.S. PATENT DOCUMENTS

| 1,081,745 | A | * | 12/1913 | Johnson et al. | ........ 128/203.25 |
| 1,356,708 | A | * | 10/1920 | Goodyear | .................. 351/156 |
| 1,443,820 | A | * | 1/1923 | Hudson | .................. 128/202.13 |
| 2,383,649 | A | * | 8/1945 | Heidbrink | ............... 128/205.25 |
| 2,414,405 | A | | 1/1947 | Blerman et al. | |
| 2,444,417 | A | * | 7/1948 | Bierman | .................. 128/201.19 |
| 2,675,803 | A | * | 4/1954 | Kaslow | ................. 128/207.11 |
| 2,765,792 | A | * | 10/1956 | Nichols | ................. 128/200.26 |
| 2,837,090 | A | | 6/1958 | Bloom et al. | |
| 3,013,556 | A | * | 12/1961 | Galleher, Jr. | ........... 128/207.11 |
| 3,065,747 | A | | 11/1962 | Forkel | |
| 3,079,917 | A | * | 3/1963 | Pate | ..................... 128/206.27 |
| 3,513,844 | A | | 5/1970 | Smith | |

(Continued)

FOREIGN PATENT DOCUMENTS

AU           156493           1/1952

(Continued)

*Primary Examiner*—Aaron J. Lewis
(74) *Attorney, Agent, or Firm*—Trexler, Bushnell, Giangiorgi, Blackstone & Marr, Ltd.

(57) ABSTRACT

A improved interface is disclosed for delivering CPAP therapy to patients. The interface has a sliding engagement to the headgear. The sliding engagement allows substantial relative lateral movement eg: when face is distorted from sleeping on side, while still providing adequate compressive force to avoid side leakage. The sliding engagement also allows easy release from the headgear.

15 Claims, 15 Drawing Sheets

U.S. PATENT DOCUMENTS

| | | | |
|---|---|---|---|
| 3,643,660 A | 2/1972 | Hudson et al. | |
| 3,792,702 A * | 2/1974 | Delest | 128/207.11 |
| 3,910,269 A | 10/1975 | Ansite et al. | |
| 3,987,798 A * | 10/1976 | McGinnis | 128/207.17 |
| 4,002,167 A * | 1/1977 | Rambosek | 128/206.24 |
| 4,106,505 A | 8/1978 | Salter et al. | |
| 4,120,300 A | 10/1978 | Tiep | |
| 4,151,843 A | 5/1979 | Brekke et al. | |
| 4,235,229 A * | 11/1980 | Ranford et al. | 128/207.17 |
| 4,414,973 A | 11/1983 | Matheson et al. | |
| 4,459,983 A | 7/1984 | Beyreuther et al. | |
| 4,641,647 A | 2/1987 | Behan | |
| 4,732,147 A * | 3/1988 | Fuller | 128/207.18 |
| 4,739,755 A | 4/1988 | White et al. | |
| 4,774,946 A | 10/1988 | Ackerman et al. | |
| 4,823,789 A | 4/1989 | Beisang, III | |
| 4,907,584 A * | 3/1990 | McGinnis | 128/206.24 |
| 5,003,632 A | 4/1991 | Claude | |
| 5,038,776 A | 8/1991 | Harrison et al. | |
| 5,042,477 A * | 8/1991 | Lewis | 128/207.17 |
| 5,042,478 A | 8/1991 | Kopala et al. | |
| 5,069,206 A * | 12/1991 | Crosbie | 128/207.17 |
| 5,074,295 A * | 12/1991 | Willis | 128/200.24 |
| 5,097,827 A | 3/1992 | Izumi | |
| 5,117,818 A | 6/1992 | Palfy | |
| 5,123,410 A * | 6/1992 | Greene et al. | 128/207.17 |
| 5,146,913 A * | 9/1992 | Khorsandian et al. | 128/200.26 |
| 5,156,641 A | 10/1992 | White | |
| 5,181,507 A * | 1/1993 | Michel et al. | 128/201.25 |
| 5,193,532 A | 3/1993 | Moa et al. | |
| 5,237,986 A * | 8/1993 | Seppala et al. | 128/201.23 |
| 5,243,971 A * | 9/1993 | Sullivan et al. | 128/205.25 |
| 5,251,616 A * | 10/1993 | Desch | 128/200.26 |
| 5,271,391 A | 12/1993 | Graves | |
| 5,282,463 A * | 2/1994 | Hammersley | 128/207.15 |
| 5,383,451 A | 1/1995 | DeIulio | |
| 5,477,852 A | 12/1995 | Landis et al. | |
| 5,513,635 A | 5/1996 | Bedi | |
| 5,533,506 A | 7/1996 | Wood | |
| 5,537,997 A * | 7/1996 | Mechlenburg et al. | 128/204.23 |
| 5,542,128 A * | 8/1996 | Lomas | 2/173 |
| 5,570,689 A * | 11/1996 | Starr et al. | 128/207.11 |
| 5,653,228 A * | 8/1997 | Byrd | 128/207.11 |
| 5,662,101 A * | 9/1997 | Ogden et al. | 128/205.25 |
| 5,682,881 A | 11/1997 | Winthrop et al. | |
| 5,687,715 A | 11/1997 | Landis et al. | |
| 5,735,272 A | 4/1998 | Dillon et al. | |
| 5,752,510 A | 5/1998 | Goldstein | |
| 5,832,918 A | 11/1998 | Pantino | |
| 5,921,239 A * | 7/1999 | McCall et al. | 128/205.25 |
| 5,975,077 A | 11/1999 | Hofstetter et al. | |
| 5,975,079 A * | 11/1999 | Hellings et al. | 128/206.24 |
| 6,019,101 A * | 2/2000 | Cotner et al. | 128/207.13 |
| 6,044,844 A * | 4/2000 | Kwok et al. | 128/207.11 |
| 6,047,699 A * | 4/2000 | Ryatt et al. | 128/207.17 |
| 6,192,886 B1 * | 2/2001 | Rudolph | 128/207.13 |
| 6,338,342 B1 | 1/2002 | Fecteau et al. | 128/207.11 |
| 6,374,826 B1 | 4/2002 | Gunaratnam et al. | 128/206.27 |
| 6,457,473 B1 * | 10/2002 | Brostrom et al. | 128/207.11 |
| 6,470,886 B1 * | 10/2002 | Jestrabek-Hart | 128/207.11 |
| 6,494,207 B1 * | 12/2002 | Kwok | 128/207.11 |
| 6,520,182 B1 * | 2/2003 | Gunaratnam | 128/206.27 |
| 6,536,435 B1 * | 3/2003 | Fecteau et al. | 128/207.11 |
| 6,536,436 B1 | 3/2003 | McGlothen | |
| 6,591,837 B1 * | 7/2003 | Byram | 128/206.24 |
| 6,612,309 B1 * | 9/2003 | Ancona | 128/207.17 |
| 6,615,834 B1 * | 9/2003 | Gradon et al. | 128/207.11 |
| 6,691,708 B1 * | 2/2004 | Kwok et al. | 128/207.11 |
| 6,701,926 B1 * | 3/2004 | Olsen et al. | 128/207.11 |
| 6,715,490 B1 * | 4/2004 | Byram | 128/206.27 |
| 6,796,308 B1 | 9/2004 | Gunaratnam et al. | |
| 6,823,869 B1 | 11/2004 | Raje et al. | |
| 6,840,238 B1 | 1/2005 | Van Hegelsom | |
| 2002/0005201 A1 | 1/2002 | Gradon et al. | |
| 2003/0000533 A1 | 1/2003 | Olsen et al. | |
| 2003/0111080 A1 | 6/2003 | Olsen et al. | |
| 2004/0112377 A1 | 6/2004 | Amarasinghe et al. | |
| 2004/0244804 A1 | 12/2004 | Olsen et al. | |
| 2005/0056286 A1 | 3/2005 | Huddart et al. | |

FOREIGN PATENT DOCUMENTS

| | | |
|---|---|---|
| EP | 1084727 | 3/2001 |
| EP | 1163924 | 12/2001 |
| WO | WO 87/03704 | 6/1987 |
| WO | WO9848876 | 11/1998 |
| WO | WO0189381 | 11/2001 |

* cited by examiner

US 7,017,576 B2

BREATHING ASSISTANCE APPARATUS

This application is a continuation application of U.S. Ser. No. 10/072,271 filed on Feb. 7, 2002 now U.S. Pat. No. 6,789,541 (now allowed), which is a continuation-in-part of U.S. Ser. No. 09/881,633 filed on Jun. 14, 2001 now U.S. Pat. No. 6,615,834 (now allowed).

FIELD OF INVENTION

This invention relates to delivery of respiratory gases particularly though not solely to patient interfaces for providing gases to patients requiring respiratory therapy.

BACKGROUND OF THE INVENTION

In the art of respiration devices, there are well known a variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

In common with prior art designs, is an inability to seal effectively when the user's face becomes distorted. For example, as shown in the prior art mask of FIG. 1 when the user 300 is sleeping on his or her side, one side 302 of the headgear tends to be pulled tight while the other side 304 tends to be loose. This causes the axis of the mask 306 to be twisted with respect to the axis of the head 308—due to the net torque from the headgear—resulting in leakage 310 on one side. The user 300 sleeping on his or her side may also distort the facial contours around the nasal area 312 and may lead to further leakage.

SUMMARY OF INVENTION

It is an object of the present invention to provide a nasal mask which goes some way to overcoming the abovementioned disadvantages in the prior art or which will at least provide the industry with a useful choice.

Accordingly in one aspect the invention consists in a device for delivering a supply of gases to a user comprising or including:

a patient interface, in use in fluid communication with said supply of gases, securement means attached to or around the head of said user, and engaging means adapted to slidingly engage said securement means with said patient interface.

In a second aspect the present invention consists in nasal mark for delivering gases to a user comprising or including:

a body portion having a inlet, in use said inlet receiving a supply of gases, sealing means engaged with said body portion, and adapted to seal against the facial contours of said user, and engaging means adapted to in use provide a sliding engagement with a means of securement to a user, and a compressive force on said sealing means to ensure said supply of gases is delivered to a user without significant leakage.

In a third aspect the present invention consists in a CPAP system for delivering gases to a user comprising or including a pressurised source of gases, transport means in fluid communication with said pressurised source adapted to convey said gases, and a patient interface in fluid communication with said transport means in use delivering said gases to said user, the improvement comprising that said patient interface adapted to sliding engage with a means of securement to a user, to ensure said supply of gases is delivered to a user without significant leakage.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

The present invention provides improvements in the field of patient interfaces for use in respiratory therapy. In particular an interface is described which is more comfortable for the user to wear and reduces the side leakage as compared with interfaces of the prior art. It will be appreciated that while a mask is described in the preferred embodiment, the present invention can be used in respiratory care generally or with a ventilator but will now be described below with reference to use in a humidified CPAP system. It will be appreciated the present invention could equally be used with any form of positive pressure respiratory therapy.

Figure 3:
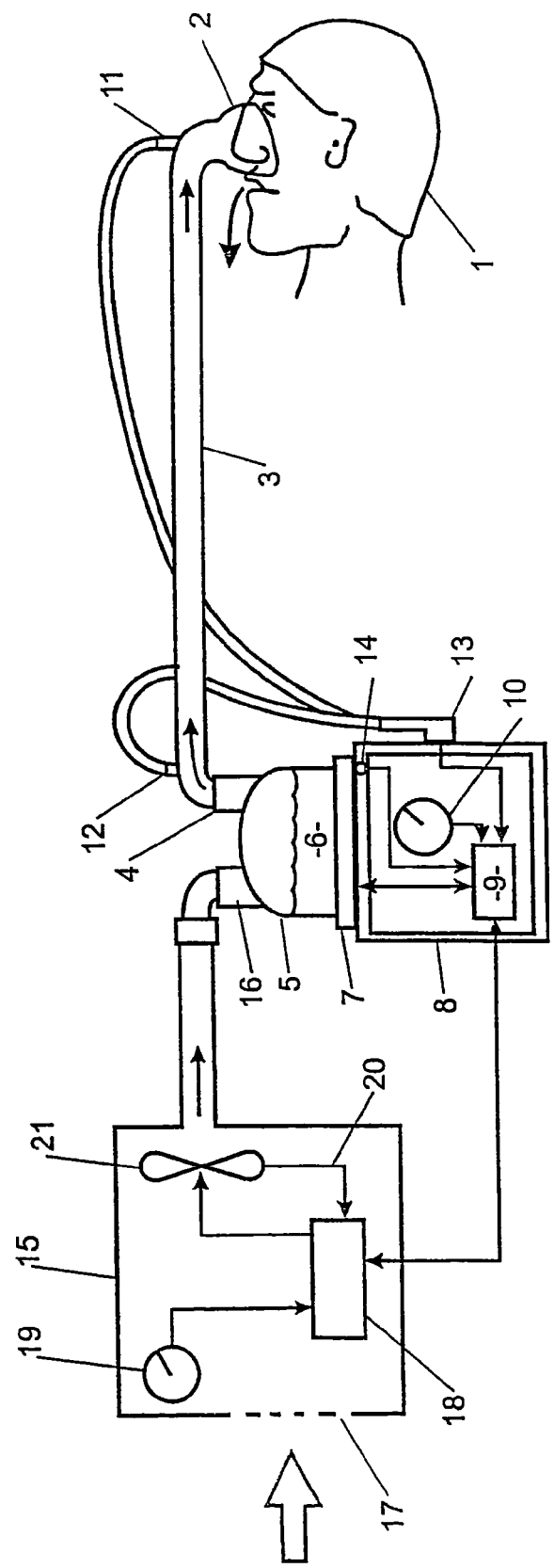
FIG. 3 is a block diagram of a humidified continuous positive airway pressure (CPAP system) as might be used in conjunction with the present invention.

With reference to FIG. 3 a humidified Continuous Positive Airway Pressure (CPAP) system is shown in which a patient 1 is receiving humidified and pressurised gases through a nasal mask 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contra a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 3.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 4:
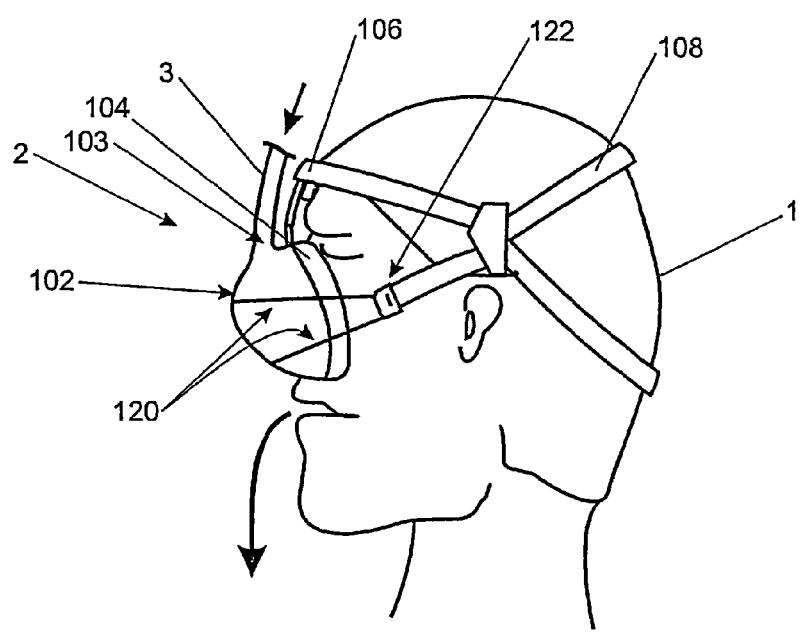
FIG. 4 is an illustration of the mask in use according to the preferred embodiment of the present invention.

Referring to FIG. 4 the nasal mask, according to the preferred embodiment of the present invention, is shown in detail. The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art

Mask Headgear

Figure 5:
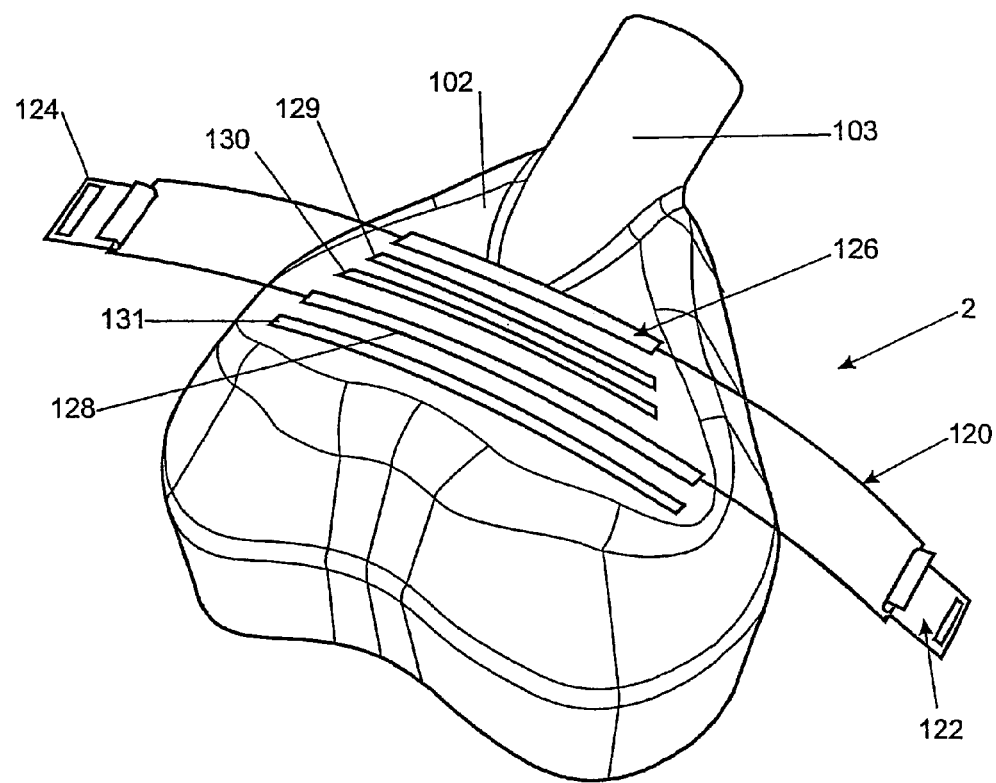
FIG. 5 is a front view of the mask illustrating the headgear securement to the mask.

Referring now to FIGS. 4 and 5 the headgear 108 is shown connected to the hollow body 102. Rather than traditional fixed or adjustable attachments the present invention utilises a sliding engagement between the headgear 108 and the hollow body 102. This is achieved in one embodiment with a loop 120, running through harnessing clips 122, 124 on either side of the headgear 108 and over the top of the hollow body 102. The loop 120 is reciprocally engaged with guides 126, 128 mounted on the top surface of the hollow body 102. The guides constrain the loop 120 but allow it to slide in and out, meaning the headgear 108 can move laterally, independently of the hollow body 102.

The advantage to this is as the face is contorted during various sleeping positions the headgear is able to move with the changes in position while the mask is left in the correct position on the nose of the user and an effective seal is maintained.

Additional guides 129, 130, 131 allow the user to adjust position of loop 120, giving ability to get different pressure on the seal depending on loop 120 position.

To further ensure user comfort and effective pressure on the mask cushion 104, the headgear 108 may be constructed either using two straps running around the back of the user's head as shown in FIG. 4 or with a partial skull cap or any other configurations as are known in the art. In this case the straps or partial skull cap would be constructed using neoprene but may also be constructed using any material as is known in the art which will be comfortable for the user.

Figure 6:
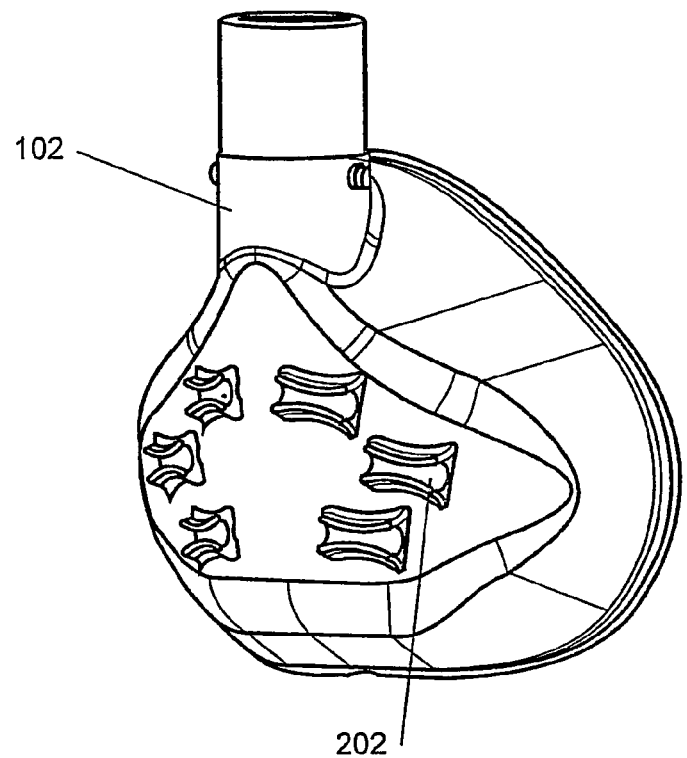
FIG. 6 is a perspective view of the mask showing multiple engaging clips.
Figure 7:
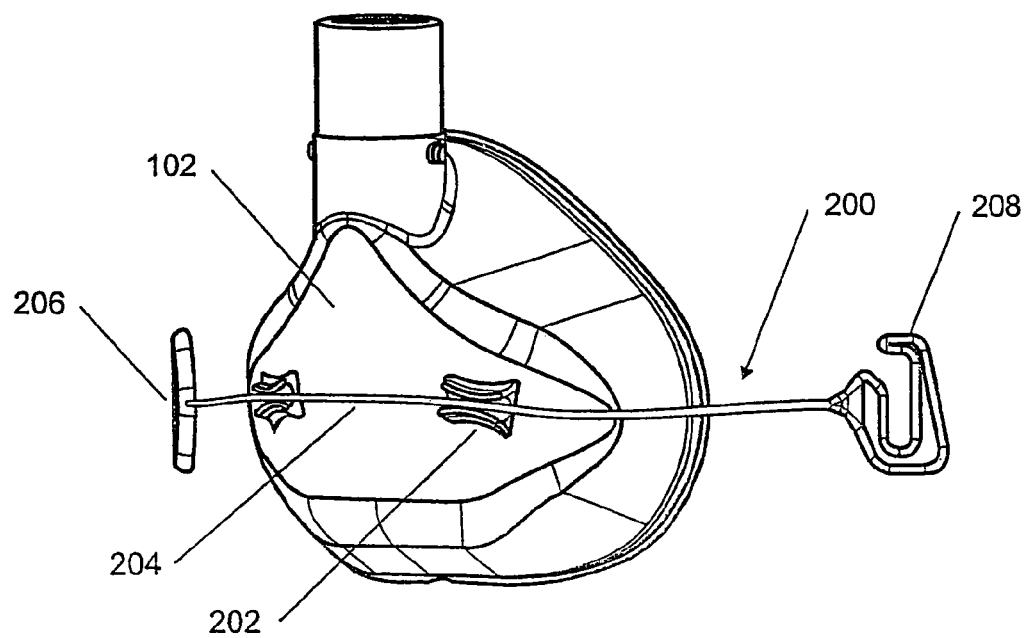
FIG. 7 is a perspective view of the mask showing the sliding strap clipped in place.
Figure 8:
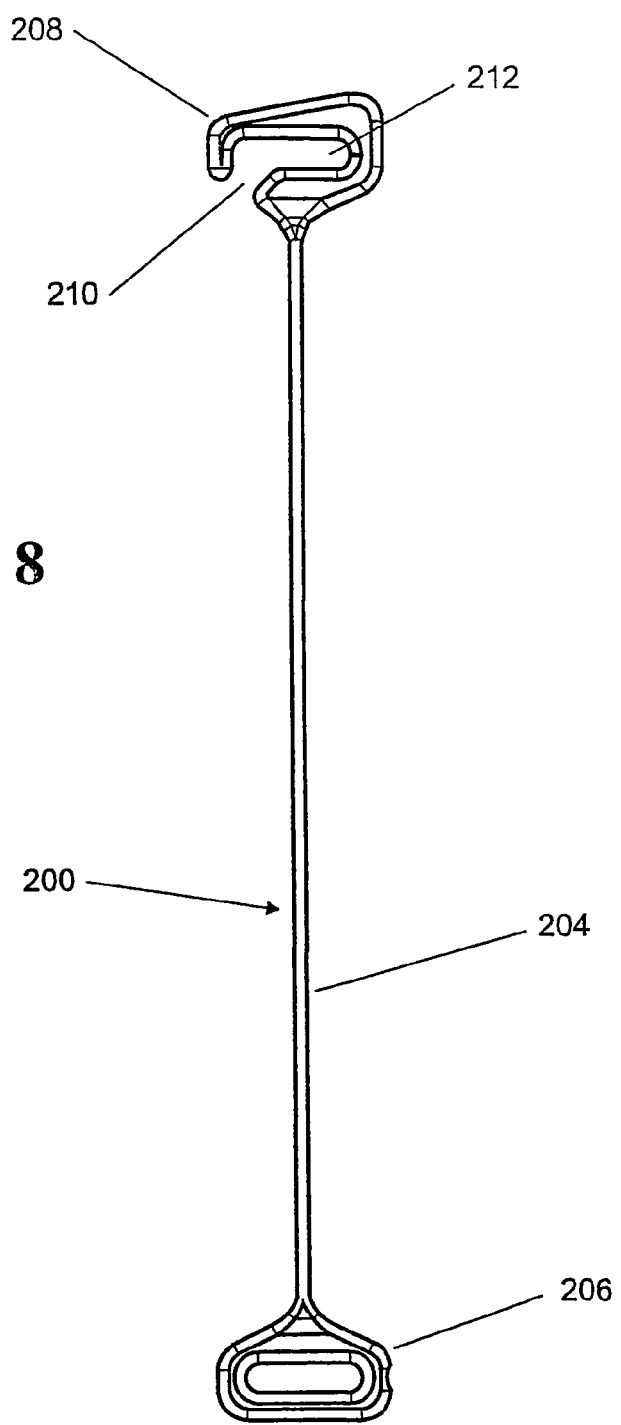
FIG. 8 is a side view of the sliding strap.

In a further embodiment shown in FIGS. 6, 7 and 8 the present invention is illustrated using a sliding strap to attach the headgear 108 to the hollow body 102. The strap 200, shown in FIG. 8 in isolation, is constructed of polyacetal (Delrin 500P NC010) using injection moulding techniques to give a polished finish. This material, similar to other nylon based derivatives, with its polished finish has a particularly low friction co-efficient, and therefore slides with respect to the hollow body 102 with very little resistance.

As shown in FIG. 6, the hollow body 102 includes a number of engaging clips 202, in use the sliding strap 200 snaps into place into the engaging clips 202 and can only be removed therefrom using a substantial force. This means that with any normal use the sliding strap 200 will stay retained within the engaging clips 202. It will also be appreciated from FIG. 6 that a number of clips are so provided, in order to allow pressure from different angles for different face shapes.

As shown in FIG. 8 the sliding strap includes a midsection 204 intended to reciprocate with the engaging clips 202, terminated at each end by loops 206, 208 which attach to the headgear 108. The first loop 206 is a full loop through which the headgear 108 is permanently attached with for example, a hook and loop strap, commonly sold under the trademark VELCRO®. The loop 208 at the other end, is only a partial loop 210 designed so that a strap or loop from the headgear 108 can be easily slipped in or out of the open section 212 to allow easy removal and attachment of the mask.

In a further alternative the sliding loop or strap could form a continuous portion of the headgear. Other variations of the sliding connection are possible, for example a clip or knob in the loop or strap could slide withing slots in the mask body.

Figure 1:
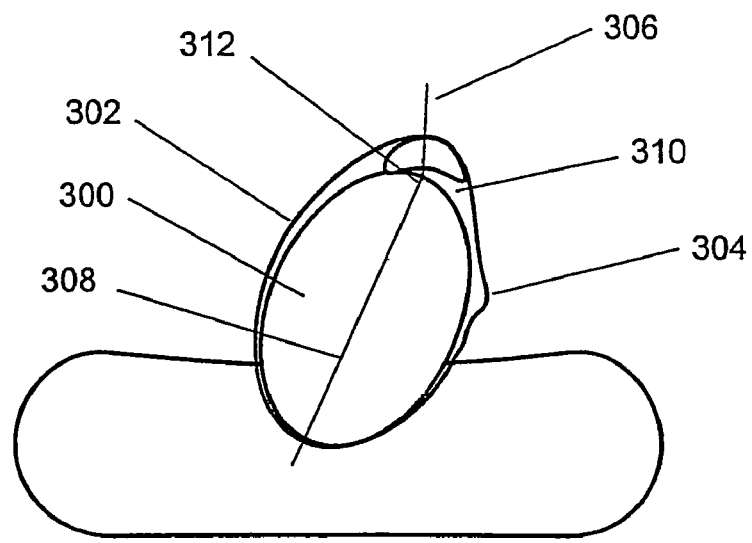
FIG. 1 is a plan view of a prior art mask illustrating side leak.
Figure 2:
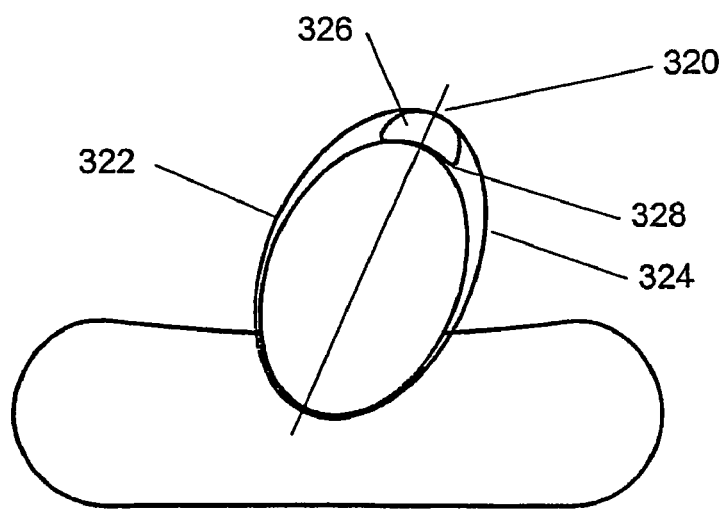
FIG. 2 is a plan view of a mask according to the preferred embodiment of the present invention.

It will be appreciated that in all embodiments of the present invention the attachment from the headgear to the mask is designed to slide with the lowest possible friction while still ensuring adequate direct force on the mask cushion to the user's face. As shown in FIG. 2 the sliding connection 320 of the present invention allows the headgear 322,324 to provide even force on both sides of the mask 326. This avoids placing a torque on the mask and consequent mask twisting, which minimises mask leaks from the seal to the face 328.

Nasal Cannula

It will be appreciated that the present invention may be equally applied to any patient interface for delivery gases to a user.

Figure 9:
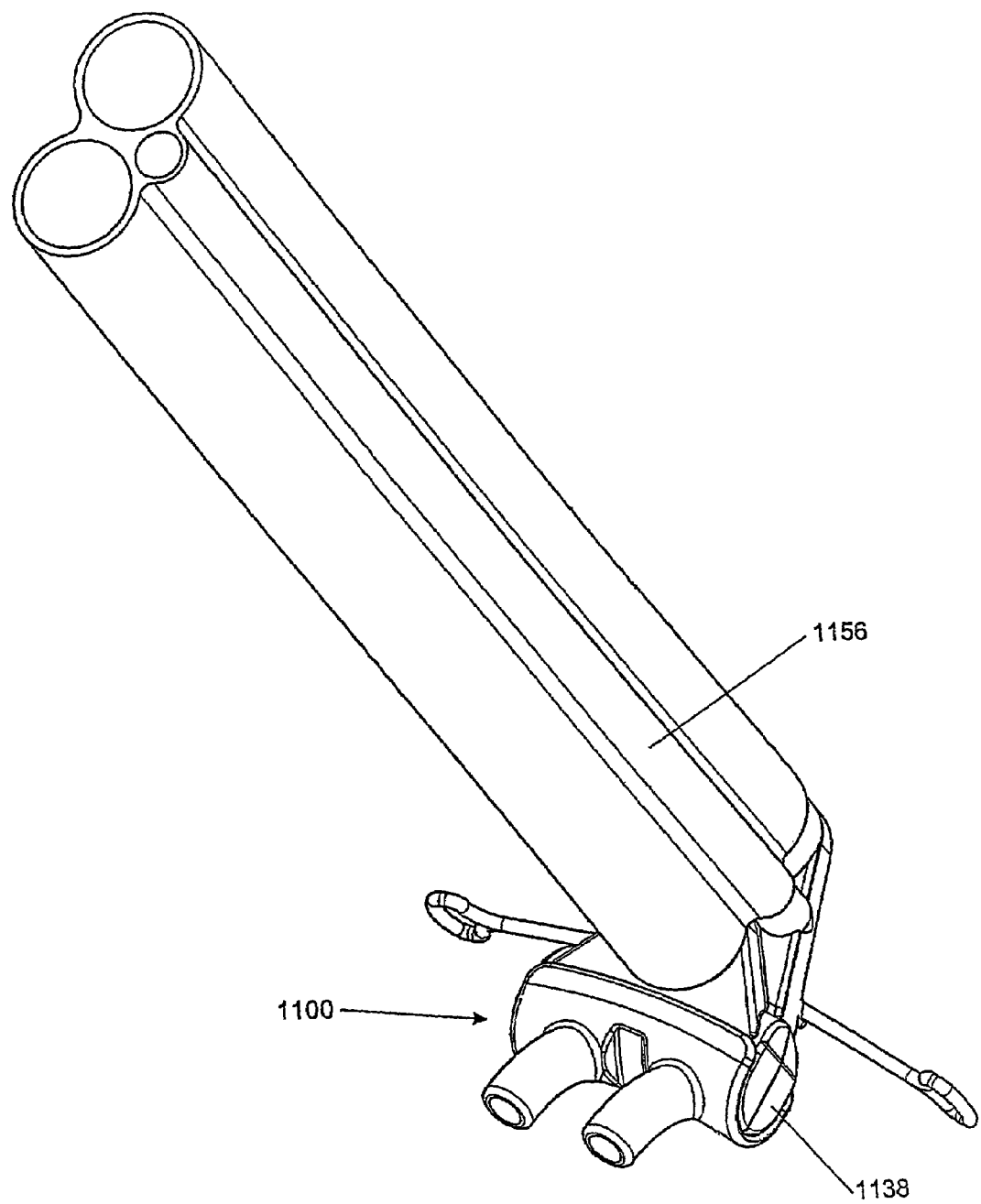
FIG. 9 is a perspective view of the cannula with the sliding strap
Figure 10:
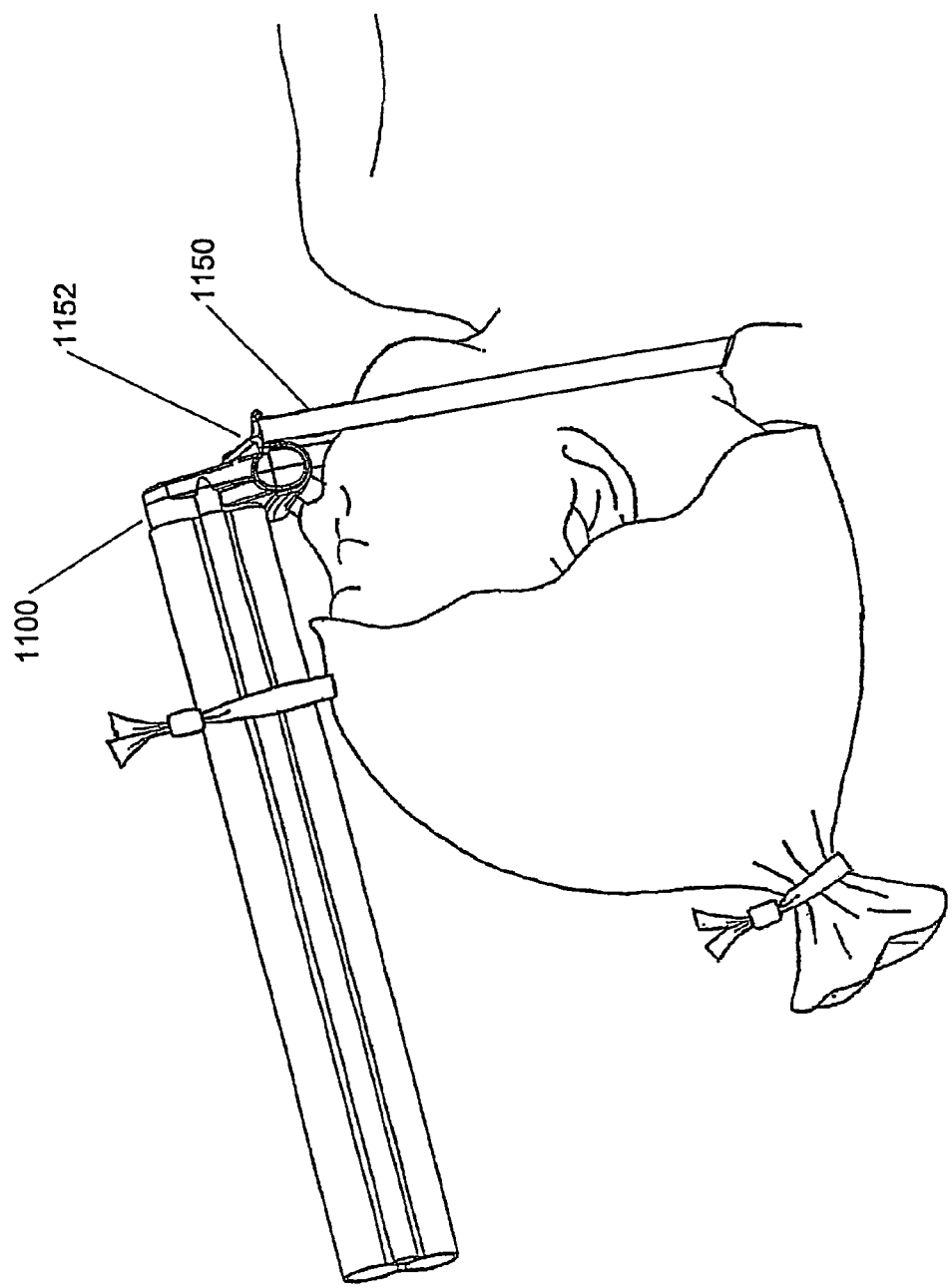
FIG. 10 is a side view of the cannula in use on a neonate.

Referring now particularly to FIGS. 9 and 10 we see that a nasal cannula 1100 is secured at its base to the back of a neonates head using strap 1150. The strap 1150 connects at the base of the neonates skull on the back of the neck. It connects to the cannula 1100 by way of a sliding strap 1152. This strap 1152 is secured by way of clips to the hard plastic body 1138 allowing the securing strap 1150 substantial relative movement with respect to the cannula 1100 as the neonate twists its head while providing adequate restraining force directly on the cannula 1100 without any twisting of the cannula 1100. In one embodiment this is accomplished by a plastic, e.g. acetal, such as one commonly sold under the trademark TEFLON®, sliding strap which engages into sliding clips on the outer face of the cannula 1100. The strap 1152 is adjustably attached to the neck strap 1150 to allow the tension to be adjusted to a comfortable level. Alternatively a sliding loop could be employed.

Full Face Mask

Referring to FIGS. 11 to 13 and 18 a number of further embodiments are illustrated particularly relating to full face masks. Similarly to the preceding embodiments in FIG. 18 the mask 1200 is attached to headgear around the head of a patient with a sliding strap 1202 which may be formed of acetal, such as one commonly sold under the trademark TEFLON®. The strap engages through a channel 1201 moulded into the mask 1200.

Figure 11:
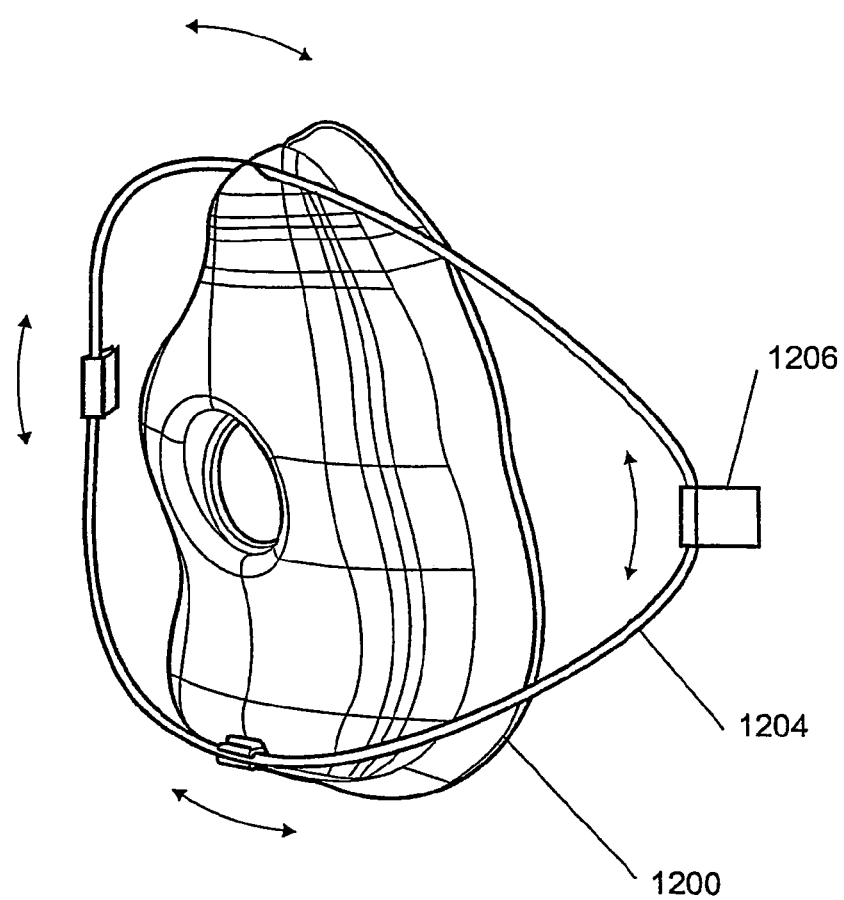
FIG. 11 is a perspective view of the fill face mask with sliding loop.
Figure 12:
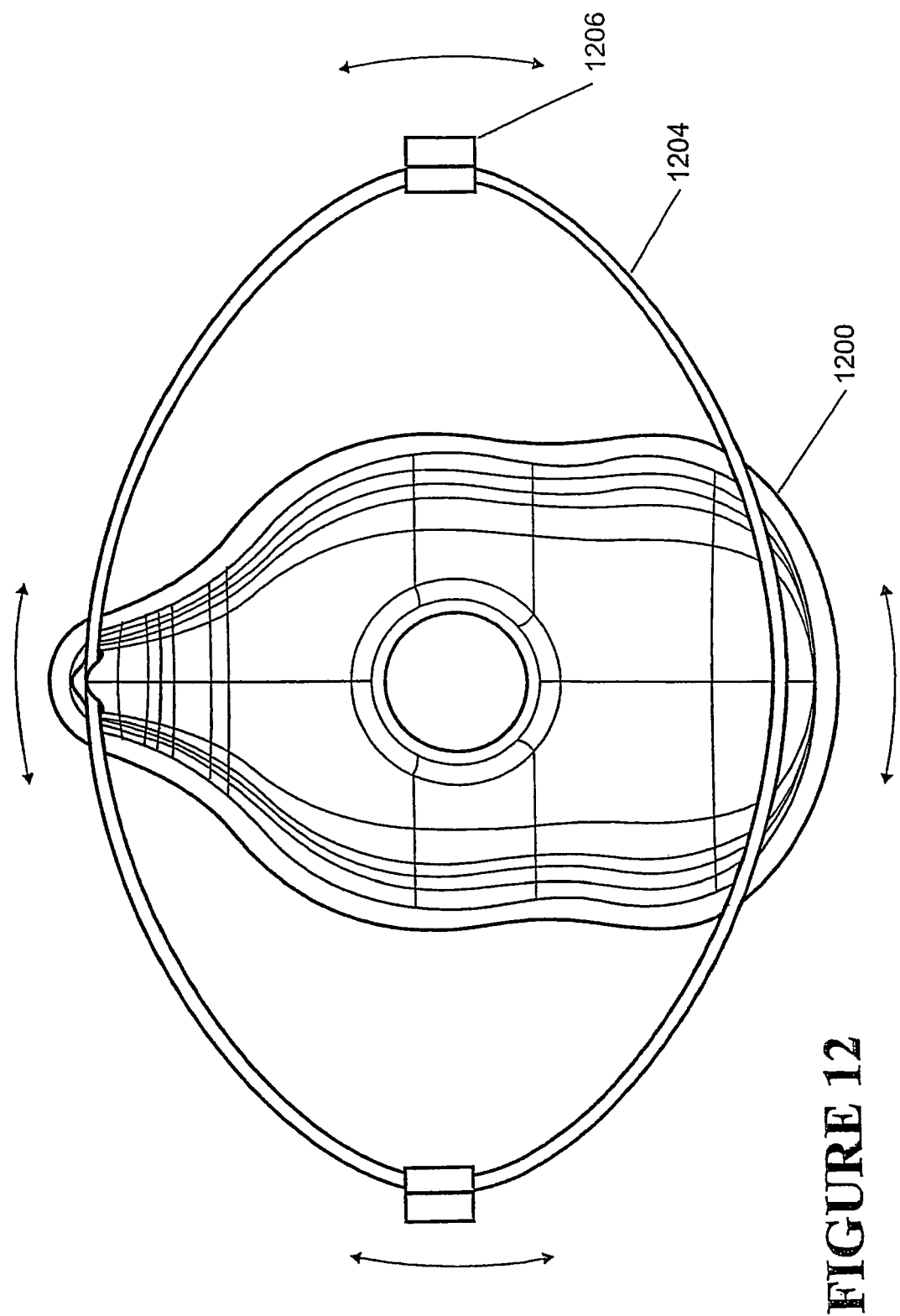
FIG. 12 is a front view of the full face mask with sliding loop.
Figure 13:
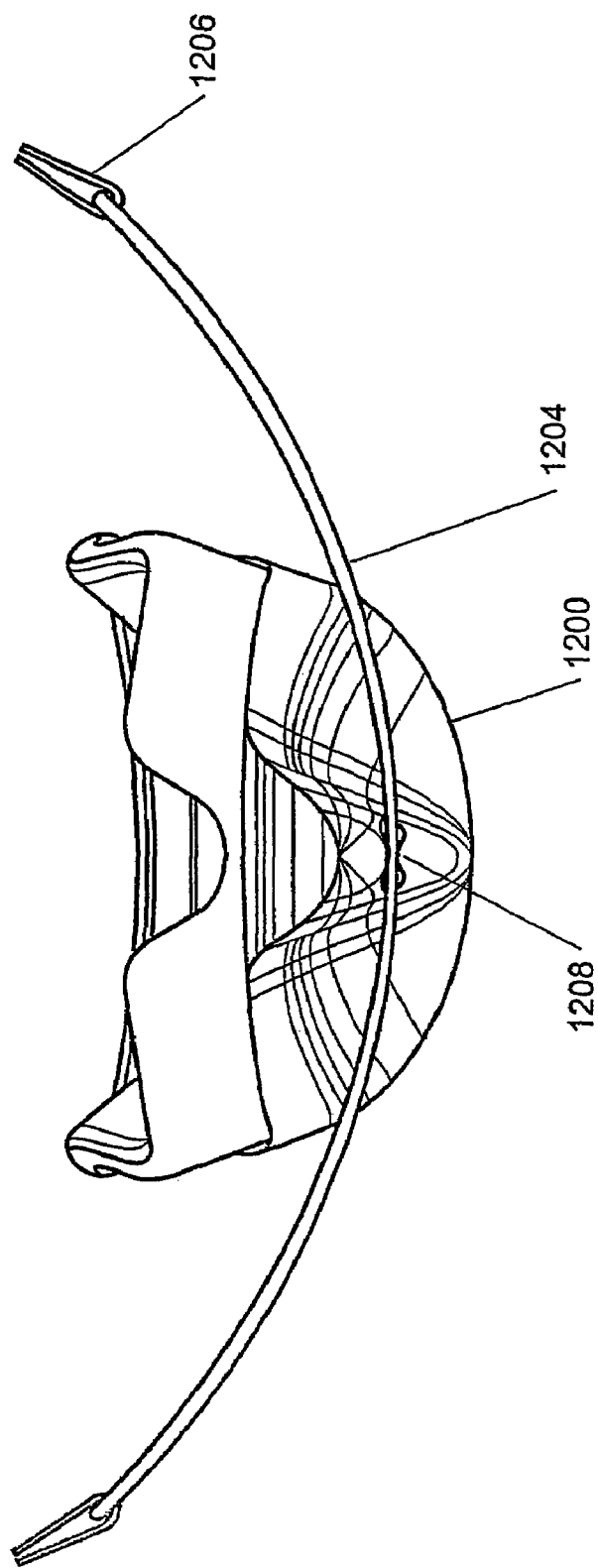
FIG. 13 is a top view of the full face mask with sliding loop.

Alternatively as seen in FIGS. 11 to 13 the mask 1200 is attached to the headgear with a sliding loop 1204. The loop 1204 engages with the headgear through loops 1206, commonly sold under the trademark VELCRO®, and to the mask 1200 through clips 1208.

Mouthpiece

Figure 14:
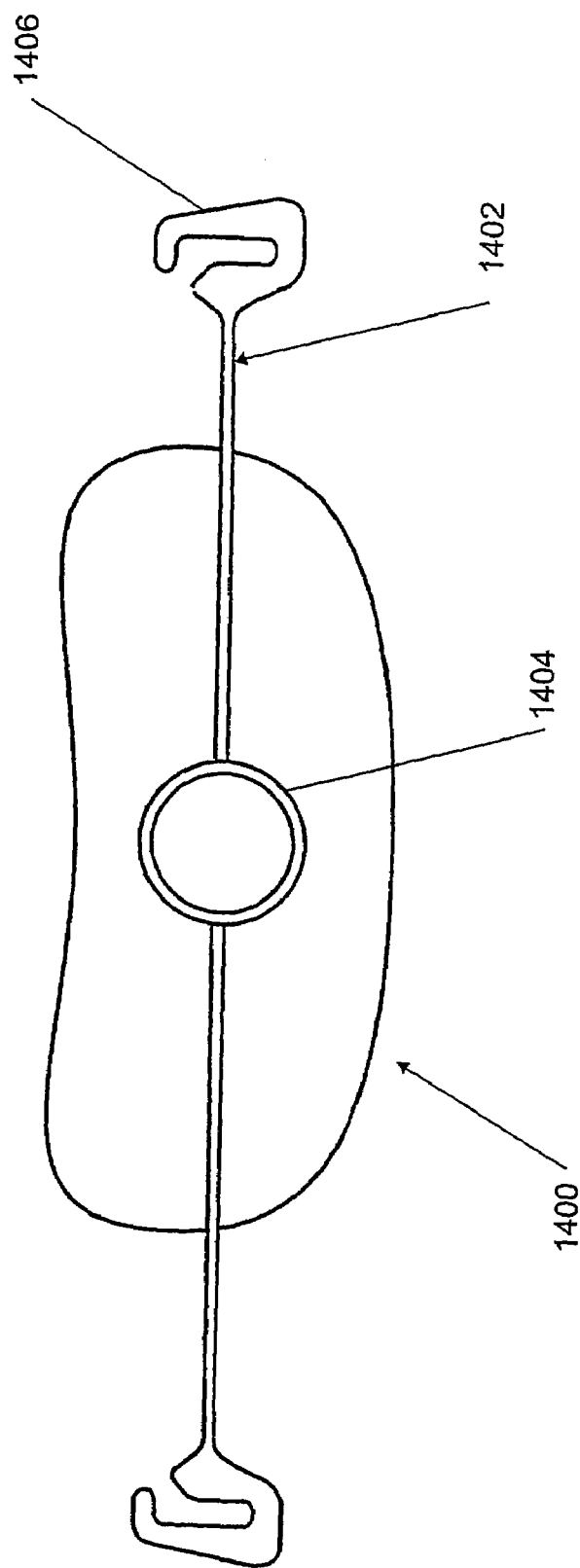
FIG. 14 is a front view of the single sliding strap on the mouthpiece.
Figure 15:
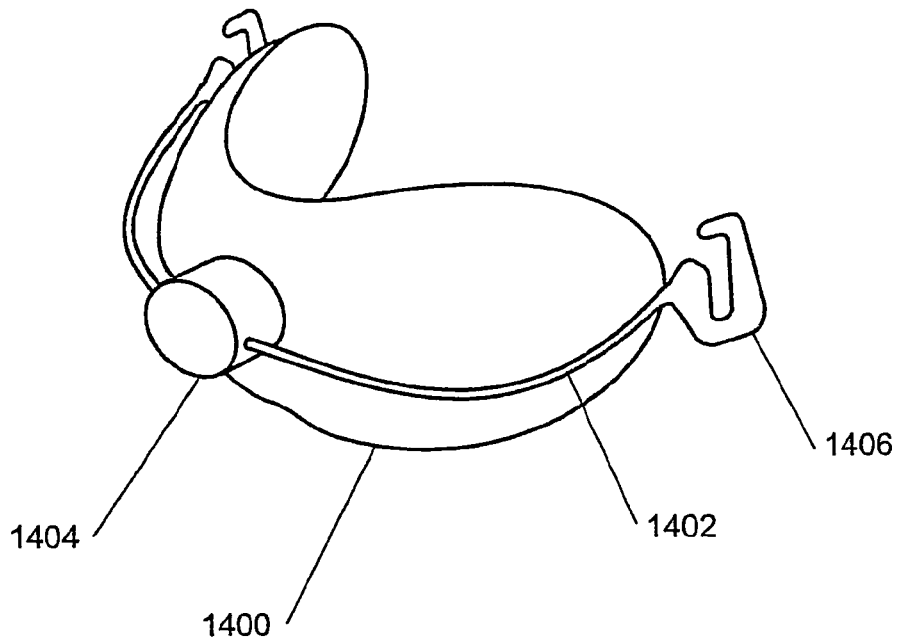
FIG. 15 is a perspective view of the single sliding strap on the mouthpiece.
Figure 16:
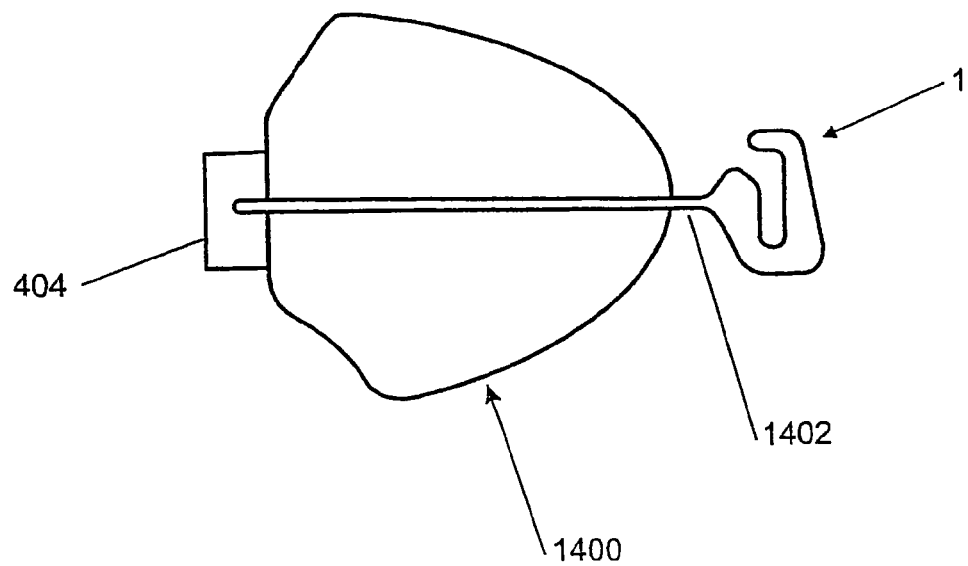
FIG. 16 is a side view of the single sliding strap on the mouthpiece.
Figure 17:
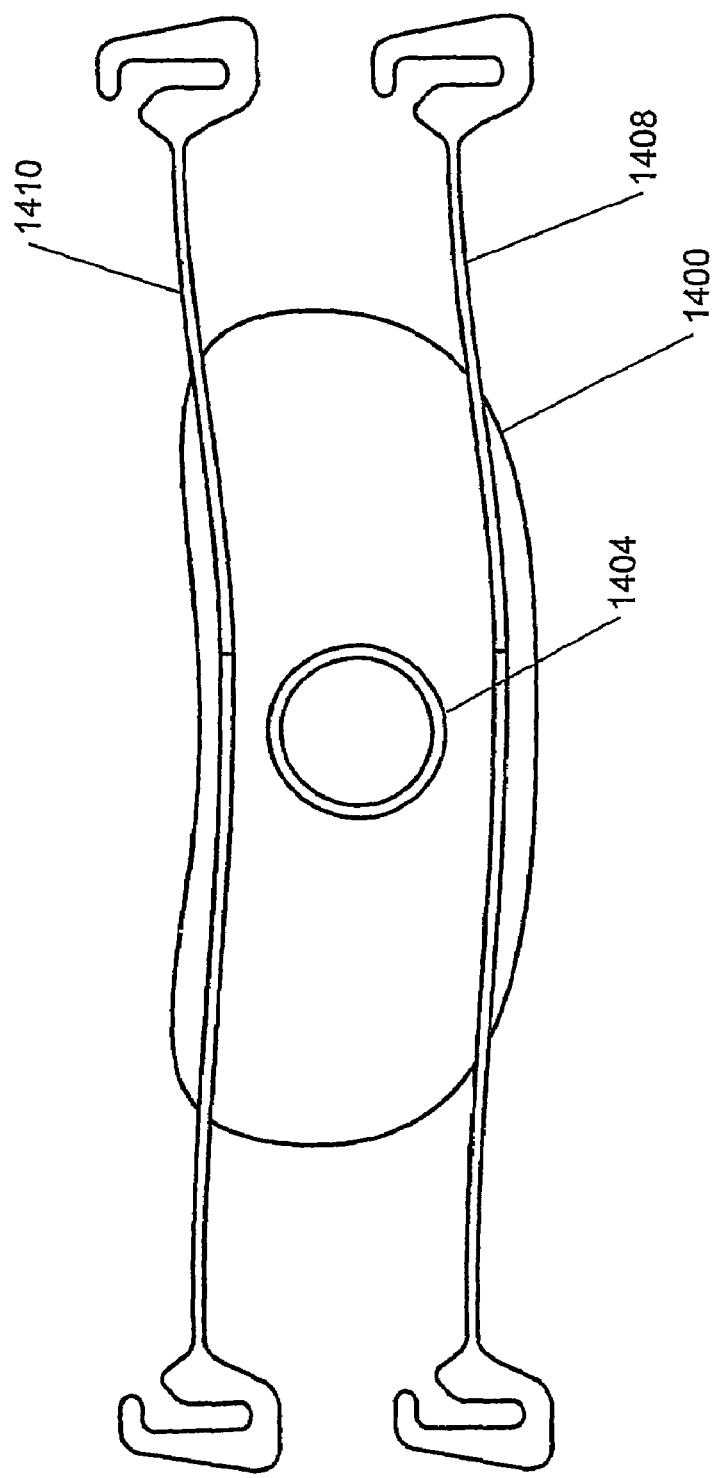
FIG. 17 is a front view of the double sliding strap on the mouthpiece.
Figure 18:
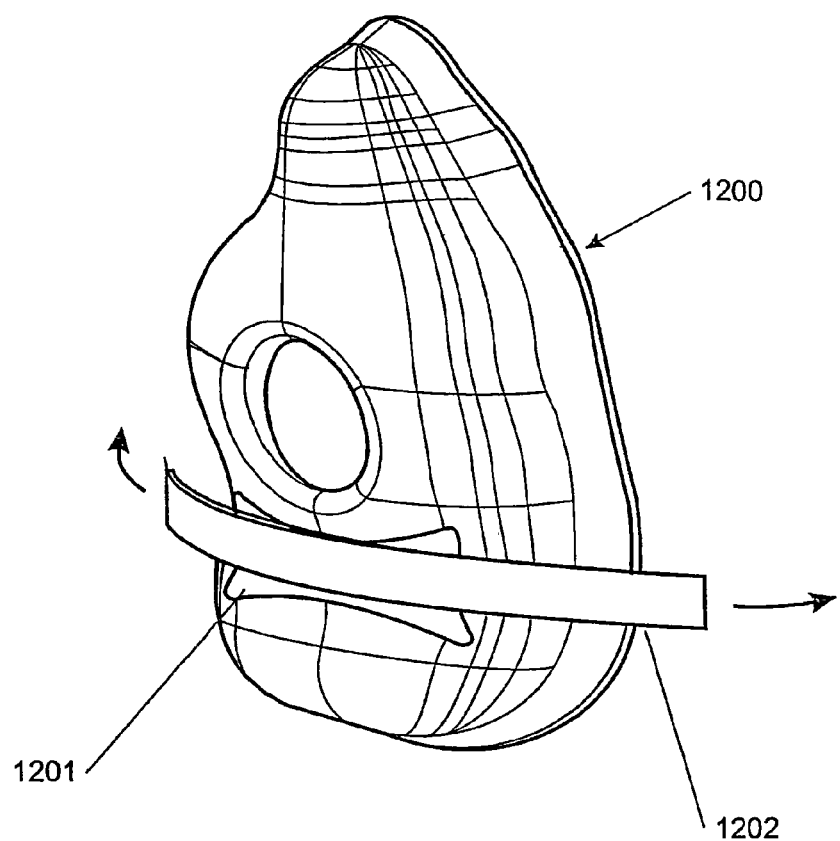
FIG. 18 is a perspective view of the sliding strap for the full face mask.

Referring to FIGS. 14 to 16 a mouthpiece 1400 is shown employing embodiments of the present invention. The mouthpiece 1400 engages with sliding strap 1402 through a channel through the inlet 1404 of the mouthpiece 1400. Again as with the preceding embodiments the strap 1402 engages to the headgear through clips 1406 at each end. In FIG. 17 two straps 1408, 1410 attach to the mouthpiece 1400 either side of the inlet 1404 in a further alternative. The mouthpiece employed could otherwise be as described in our European Patent Application No. 1163924 or other mouthpieces as would be contemplated by one skilled in the art.

It will be appreciated that numerous other interfaces for example E.T (endrotraceal) tubes might also be used in conjunction with the present invention.

What is claimed is:

1. A device for delivering a supply of gases to a user comprising or including:
    a patient interface, adapted to be in fluid communication with said supply of gases and said user, said patient interface being in at least a correct orientation and position on said user,
    headgear adapted to attach to or around the head of said user, and
    a flexible sliding strap attached to said headgear and capable of sliding over said patient interface.

2. A device as claimed in claim 1 wherein said patient interface is a nasal mask.

3. A device as claimed in claim 2 wherein said nasal mask comprises or includes a body portion having an inlet receiving said supply of gases, and sealing means attached to or integrated with said body portion said sealing means adapted to seal against the facial contours of said user.

4. A device as claimed in claim 3 where said sliding strap is a low resistance strap slidingly connected with said patient interface and adapted to allow said headgear substantial movement with respect to said nasal mask, while still providing compressive force on said sealing means to ensure said supply of gases is delivered to said user without significant leakage.

5. A device as claimed in claim 3 wherein said patient interface further comprises or includes at least one restraining means on said body portion, said restraining means adapted to in use restrain said strap, but allow said strap to slide longitudinally over said patient interface, said restraining means adapted to in use easily disengage with said sliding strap.

6. A device as claimed in claim 1 wherein said strap is elongate having a first end and a second end, a first at least partial loop located at said first end and a second at least partial loop located at said second end, whereby in use said headgear is substantially permanently attached to said first loop and substantially attached but readily releasable from said second loop.

7. A device as claimed in claim 1 wherein said patient interface is a nasal cannula.

8. A device as claimed in claim 1 wherein said patient interface is a full face mask.

9. A device as claimed in claim 1 wherein said patient interface is a mouthpiece.

10. A device as claimed in claim 1 wherein said patient interface is an entrotracheal tube.

11. A device as claimed in any one of claims 7 to 10 wherein said heargear includes a low resistance sliding loop slidingly connected on, through, adjacent or with said patient interface.

12. A device as claimed in claim 11 wherein said sliding loop comprises a looped nylon filament.

13. A device as claimed in claim 1 wherein said sliding strap is moulded from polyacetal.

14. A nasal mask for delivering gases to a user comprising or including:
    a body portion having an inlet, in use said inlet receiving a supply of gases, headgear adapted to attach to or around the head of said user abutting means engaged with said body portion for abutting against the facial contours of said user, a flexible sliding strap capable of sliding over said nasal mask and attaching to said headgear, and engaging means for providing a sliding engagement with said sliding strap, and a compressive force on said abutting means.

15. A nasal mask as claimed in claim 14 wherein said engaging means comprises or includes restraining means to in use restrain said strap but allow said strap to slide longitudinally over said patient interface, said restraining means adapted to in use easily disengage with said sliding strap.

\* \* \* \* \*

UNITED STATES PATENT AND TRADEMARK OFFICE
CERTIFICATE OF CORRECTION

| | |
|---|---|
| PATENT NO. | : 7,017,576 B2 |
| APPLICATION NO. | : 10/646434 |
| DATED | : March 28, 2006 |
| INVENTOR(S) | : Olsen et al. |

It is certified that error appears in the above-identified patent and that said Letters Patent is hereby corrected as shown below:

Column 3, Line 27 "5 which contra" should be
-- 5 which contains --

Column 6, Line 57 "said heargear" should be
-- said headgear --

Signed and Sealed this

Eleventh Day of July, 2006

JON W. DUDAS
*Director of the United States Patent and Trademark Office*